United States Patent [19]
Geissler et al.

[11] Patent Number: 6,002,020
[45] Date of Patent: Dec. 14, 1999

[54] PROCESS FOR THE CATALYTIC PREPARATION OF 3-ISOCHROMANONES FROM PHTHALANS

[75] Inventors: Holger Geissler, Mainz; Daniel Decker, Sulzbach; Peter Gross, Kelsterbach, all of Germany

[73] Assignee: Clariant GmbH, Frankfurt, Germany

[21] Appl. No.: 09/239,001

[22] Filed: Jan. 27, 1999

[30] Foreign Application Priority Data

Jan. 28, 1998 [DE] Germany .................. 198 03 076

[51] Int. Cl.$^6$ .................. C07D 311/10; C07D 311/14; C07D 311/16
[52] U.S. Cl. .................. 549/290; 549/283; 549/288; 549/289
[58] Field of Search .................. 549/290, 283, 549/288, 289

[56] References Cited

U.S. PATENT DOCUMENTS 5,663,370 9/1997 Bowden et al. .................. 549/290

OTHER PUBLICATIONS

XP–002103592 "Reductive Electrophillic Substitution of Phthalans and Ring Expansion to Isochroman Derivatives," U. Azzena, S. Demartis, M. Fiori, G. Melloni and L. Pisano, Tetrahedron Letters, vol. 36, No. 44, pp. 8123–8126, 1995.

XP–002103591 "1,2–Di (lithiomethyl) benzene From Phthalan: Sequential Introduction of Two Different Electrophiles,"J. Almena, F. Foubelo and M. Yus, Tetrahedron, vol. 51, No. 11, pp. 3351–3364, 1995.

*Primary Examiner*—Ba K. Trinh
*Attorney, Agent, or Firm*—Scott E. Hanf

[57] ABSTRACT

Good yields and selectivities are achieved in a process for preparing an isochroman-3-one of the formula (I)

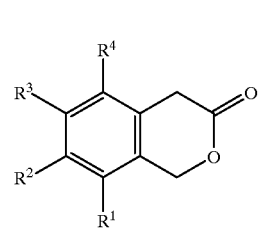

(I)

by reacting a 1,3-dihydroisobenzofuran of the formula (II)

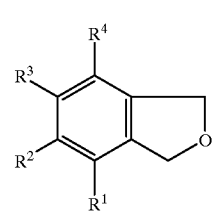

(II)

with carbon monoxide at a CO pressure of from 0.1 to 20 MPa in the presence of an ionic halide, a palladium catalyst and a dipolar aprotic solvent.

15 Claims, No Drawings

PROCESS FOR THE CATALYTIC PREPARATION OF 3-ISOCHROMANONES FROM PHTHALANS

CROSS-REFERENCES TO RELATED APPLICATIONS

The present invention is described in the German priority application No. 198 03 07602, filed Jan. 28th 1998, which is hereby incorporated by reference as is fully disclosed herein.

BACKGROUND OF THE INVENTION

The present invention relates to a novel process for the catalytic preparation of 3-isochromanones from phthalans.

3-Isochromanones and their substituted derivatives are of great interest, for example, as intermediates in the synthesis of pharmaceuticals and crop protection agents. Thus, EP-A-0 278 595 and WO 97/12864 describe the use of 3-isochromanone as an intermediate in the synthesis of fungicides and pesticides.

3-Isochromanones are prepared from phthalans by the process of Azzena et al. (Tetrahedron Lett. 1995, Vol. 36, page 8123ff), Almena et al. (Tetrahedron 1995, Vol. 51, p. 3351ff) and Churanov et al. (Vestn. Mosk. Univ., Khim 1975, Vol. 16, 338 ff.). To this end, the corresponding 1,3-dihydroisobenzofurans (phthalans) are reacted with lithium and catalytic amounts of naphthalene to give the dilithium compound of the formula below

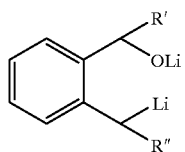

which is subsequently converted into the desired 3-isochromanone by reaction with carbon dioxide.

This process requires two equivalents of metallic lithium per equivalent of product.

The consequence of this high consumption of lithium is that transfer of this process to industrial scales is uneconomical, in particular owing to the safety precautions associated with metallic lithium and especially owing to the high costs.

SUMMARY OF THE INVENTION

It is an object of the present invention to provide a novel process for the synthesis of 3-isochromanones which avoids the above-described disadvantages of the prior art.

DESCRIPTION OF THE PREFERRED EMBODIMENTS

This object is achieved by a process for the preparation of an isochroman-3-one of the formula (I)

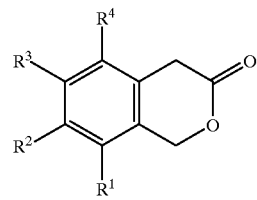

by reacting a 1,3-dihydroisobenzofuran of the formula (II)

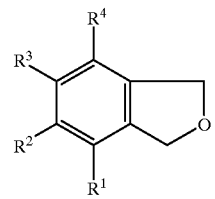

with carbon monoxide at a CO pressure of from 0.1 to 20 MPa in the presence of an ionic halide, a palladium catalyst and a dipolar aprotic solvent; where in the formulae (I) and (II) the radicals $R^1$, $R^2$, $R^3$ and $R^4$ independently of one another are:

a hydrogen or fluorine atom;

an $HO_2CCH=CH-$, $H_2NC(=O)-$, $HC(=O)NH-$, $CN-$ or $CF_3-$ group;

an alkyl, alkoxy or acyloxy radical having in each case 1 to 18 carbon atoms; or a $C_6-C_{18}$-aryloxy, aryl or heteroaryl radical, the heteroatoms being 1 to 3 atoms from the group consisting of O, N and S;

an $R^5C(=O)NH-$, $R^5OC(=O)NH-$, $R^5C(=O)R^5N-$, $R^5{}_2P(=O)-$, $R^6{}_2N-$, $R^6C(=O)-$, $R^6OC(=O)-$, $R^6OC(=O)CH=CH-$, $R^7C(=O)-$, $R^7{}_2N-$, $R^7OC(=O)CH=CH-$ or $R^7{}_2P(=O)-$ radical; in which $R^5$ is a $C_1-C_4$-alkyl radical, $R^6$ is a $C_1-C_{18}$-alkyl radical and $R^7$ is a $C_6-C_{18}$-aryl radical; or in which at least one of the radicals $R^1$, $R^2$, $R^3$ and $R^4$ is substituted by a radical $R^9$, where $R^9$ has the same meaning as $R^1$; or in which at least two of the radicals $R^1$, $R^2$, $R^3$ and $R^4$ are linked to one another and form at least one aliphatic or aromatic ring having 5 to 18 carbon atoms.

$R^1$, $R^2$, $R^3$ and $R^4$ are preferably hydrogen, fluorine, methyl, ethyl, methoxy or ethoxy.

The ionic halide is preferably employed in an amount of from 1 to 50 mol %, in particular from 2 to 10 mol %, based on the compound of the formula (II). The palladium catalyst is preferably employed in an amount of from 0.0001 to 1 mol %, in particular from 0.01 to 0.5 mol %, based on the compound of the formula (II).

A suitable dipolar aprotic solvent can be selected from the group consisting of dioxane, tetrahydrofuran, N-($C_1-C_{18}$-alkyl)pyrrolidone, ethylene glycol dimethyl ether, ethyl acetate, acetonitrile, tert-butyl methyl ether, dibutyl ether, sulfolane and N,N-dimethylacetamide. Particular preference is given to N-methylpyrrolidone, N-octylpyrrolidone, N-dodecylpyrrolidone and N,N-dimethylacetamide. These solvents can be employed both in pure form and in a product-containing form or product-saturated form. The latter variant is preferably used in a continuous process.

The use of high-boiling solvents, such as N-octylpyrrolidone or N-dodecylpyrrolidone, in the preparation of 3-isochromanones having a boiling point lower than that of the solvent, such as, for example, pure 3-isochromanone, has the advantage that the product and unreacted starting material can be distilled off directly from the reaction medium. If supported palladium catalysts are used, it has proven to be advantageous to remove the catalyst beforehand by filtration. The distillation bottom can be reused for further reactions. This variant is particularly suitable for effective catalyst and solvent recycling.

In principle, any amount of solvent can be employed; however, it is expedient to use from 0.1 to 2.5 molar solutions of the compound of the formula (II) in the solvent.

The ionic halide can be an alkali metal, ammonium or phosphonium halide, halide being chloride, bromide or iodide.

Preference is given to using the ionic halide ammonium bromide, lithium bromide, sodium bromide, potassium bromide, tetrabutylphosphonium bromide, ammonium chloride, lithium chloride, sodium chloride, potassium chloride, tetrabutylphosphonium chloride, ammonium iodide, lithium iodide, sodium iodide, potassium iodide, tetrabutylphosphonium iodide or a combination thereof.

The catalyst can comprise both metallic palladium and a palladium(II) compound, either in unsupported form (neat catalyst) or preferably as a supported substance (metallic palladium or a palladium compound applied to a support).

Particularly suitable supports are activated carbon, metal oxides, metal salts, such as, for example, sulfates or carbonates of the elements of the second and the third main group and the first and the third sub-group of the Periodic Table of the Elements, such as, for example, aluminum oxide, barium sulfate, calcium carbonate and/or silicon dioxide. A particularly preferred support is activated carbon. These supports can be employed in the process according to the invention both on their own and in mixed form.

Palladium(II) compounds which may be used are in particular $PdCl_2$, $PdBr_2$ or $Pd(OAc)_2$.

In a preferred embodiment, the palladium catalyst additionally comprises a ligand, in particular a phosphine compound.

Particularly suitable for the process according to the invention are catalysts comprising a bis(phosphine) palladium(II) compound. These complexes can be employed either in a commercially available form or be obtained by reaction of a palladium(II) compound, such as, for example, $PdBr_2$, $PdCl_2$ or palladium(II) acetate, with the appropriate phosphines. The phosphine compound here can be triphenylphosphine, tritolylphosphine, bis(diphenylphosphino)ethane, 1,4-bis(diphenylphosphino)butane or 1,3-bis(diphenylphosphino)propane. Particular preference is given to using bis(triphenylphosphine) palladium(II) bromide of the formula $PdBr_2[PPh_3]_2$ or bis(triphenylphosphine)palladium(II) chloride of the formula $PdCl_2[PPh_3]_2$ as catalyst. This complex can be prepared by reacting palladium(II) bromide or palladium(II) chloride and triphenylphosphine.

Using phosphines having one or more chiral centers, it is possible to obtain pure enantiomers or a product which is enriched with one enantiomer.

It is also possible to employ mixtures of the catalysts described above.

In a further preferred embodiment, the reaction is carried out in the presence of an inorganic or organic acid having a pKa of less than 5, the acid preferably being present in an amount of from 0.1 to 5 mol %, particularly preferably from 1 to 2.5 mol %, based on the compound of the formula (II). Particularly suitable acids are sulfuric acid, phosphoric acid, p-toluenesulfonic acid, hexafluoropropanoic acid and trifluoroacetic acid.

However, it is also possible to carry out the reaction in the presence of a cationic ion exchange resin. Particularly suitable for this purpose are Amberlyst® 15 (registered trademark of Rohm and Haas; CAS-No. 9037-24-5) or Nafion® (registered trademark of DuPont; CAS-No. 31175-20-9). Preference is given to using sulfuric acid.

The reaction according to the invention is carried out at a carbon monoxide pressure between 0.1 and 20 MPa, preferably between 1 and 10 MPa, and at a temperature of preferably between 20 and 200° C., in particular between 50 and 150° C.

The reaction according to the invention proceeds with high selectivity and good yield, without any byproduct formation worth mentioning.

EXAMPLES

Example 1 (Comparative Example)

75.0 g of phthalan (1,3-dihydroisobenzofuran) and 100 mg of sulfuric acid are successively mixed under an atmosphere of protective gas (argon) in a 200 ml autoclave made from V4A steel. Carbon monoxide is subsequently applied at a pressure of 60 bar, and the temperature is then incrreased to 130° C. After a reaction time of 6 hours at 130° C., the mixture is cooled. Gas chromatographic analysis shows that the reaction mixture does not contain any 3-isochromanones. 1 g of activated carbon containing 30% by weight of palladium (30% palladium on activated carbon) is subsequently added to the autoclave, the autoclave is closed and carbon monoxide is applied at a pressure of 60 bar. The temperature is increased to 130° C. After a further reaction time of 6 hours at 130° C., the mixture is cooled. A second gas chromatographic analysis shows that the reaction mixture again does not contain any 3-isochromanones.

Example 2

24.0 g of phthalan (1,3-dihydroisobenzofuran), 100 ml of N-methylpyrrolidone (NMP), 1 g of 30% palladium on activated carbon, 3.00 g of lithium bromide and 100 mg of sulfuric acid are successively mixed under an atmosphere of protective gas (argon) in a 200 ml autoclave made from V4A steel. Carbon monoxide is subsequently applied at a pressure of 60 bar, and the temperature is then increased to 130° C. After a reaction time of 6 hours at 130° C., during which the carbon monoxide pressure is maintained at between 70 and 80 bar by applying pressurized carbon monoxide, the mixture is cooled. Gas-chromatographic analysis shows that the reaction mixture contains 12.5 g of 3-isochromanone, corresponding to a yield of 43%. The selectivity is higher than 95%.

For work-up of the product, the palladium on activated carbon is filtered off after cooling. The solvent and unreacted phthalan are subsequently evaporated off in a thin-layer evaporator at 100° C. and 10 mbar. The solvent (NMP) which is recovered in this manner and which contains unreacted phthalan can be reused for a new reaction.

The residue containing the 3-isochromanone is admixed with water. An oil containing 3-isochromanone and phthalan in a ratio of 5:1 separates off. This oil is taken up in 3 equivalents by volume of tert-butyl methyl ether (MTBE), separated off and dried using sodium sulfate. The tert-butyl methyl ether is evaporated off, and the residue is then admixed with 2 equivalents by volume of hexane, after which the phthalan dissolves and the 3-isochromanone crystallizes out of the solution. Filtration with suction gives 12.0 g of 3-isochromanone having a melting point of 79 to 80° C.

$^1$H NMR (300 MHz, CDCl$_3$): δ=7.20–7.40 (m, 4H), 5.31 (s, 2H), 3.71 (s, 2H).

Example 3

Similarly to Example 1, 24.0 g of phthalan (1,3-dihydroisobenzofuran), 100 ml of N-methylpyrrolidone (NMP), 1 g of 30% palladium on activated carbon, 3.00 g of lithium bromide and 100 mg of sulfuric acid are successively reacted in a 200 ml autoclave made from V4A steel.

For work-up, the palladium on activated carbon is filtered off after cooling. The solvent and unreacted phthalan are subsequently evaporated off in a thin-layer evaporator at 100° C. and 10 mbar. 20 g of NMP are subsequently added and once more evaporated off in the thin-layer evaporator at 100° C. and 10 mbar, so that the phthalan which is not evaporated is removed almost completely from the residue. The residue which contains the 3-isochromanone is admixed with water. The 3-isochromanone separates off as a solid. Filtration with suction gives 12.3 g of 3-isochromanone having a melting point of 80–81° C. The yield is 42%, the selectivity is higher than 95%.

Examples 4 to 12

These examples are carried out similarly to Example 2. The starting materials and their quantities and the reaction results are shown in Table 1.

In Table 1, the following terms are used:

in the solvent column, "NMP" is N-methylpyrrolidone and "DMAC" is N,N-dimethylacetamide;

in the catalyst column, "30% Pd on C" is activated carbon containing 30% by weight of palladium (30% palladium on activated carbon);

in the acid column H$_2$SO$_4$ is 96% strength sulfuric acid;

CO denotes the carbon monoxide pressure range at a reaction temperature of 130° C.

We claim:
1. A process for the preparation of an isochroman-3-one of the formula (I)

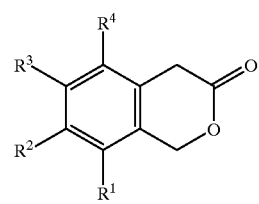

(I)

by reacting a 1,3-dihydroisobenzofuran of the formula (II)

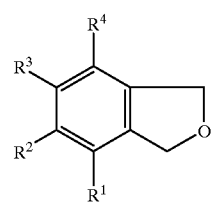

(II)

with carbon monoxide at a CO pressure of from 0.1 to 20 MPa in the presence of an ionic halide, a palladium catalyst and a dipolar aprotic solvent; where in the formulae (I) and (II) the radicals R$^1$, R$^2$, R$^3$ and R$^4$ independently of one another are:

a hydrogen or fluorine atom;

an HO$_2$CCH=CH—, H$_2$NC(=O)—, HC(=O)NH—, CN— or CF$_3$— group;

an alkyl, alkoxy or acyloxy radical having in each case 1 to 18 carbon atoms; or a C$_6$–C$_{18}$-aryloxy, aryl or heteroaryl radical, the heteroatoms being 1 to 3 atoms from the group consisting of O, N and S;

an R$^5$C(=O)NH—, R$^5$OC(=O)NH—, R$^5$C(=O) R$^5$N—, R$^5{}_2$P(=O)—, R$^6{}_2$N—, R$^6$C(=O)—, R$^6$OC (=O)—, R$^6$OC(=O)CH=CH—, R$^7$C(=O)—, R$^7{}_2$N—, R$^7$OC(=O)CH=CH— or R$^7{}_2$P(=O)— radi-

TABLE 1

| Ex. | Phthalan [in g] | Solvent [in ml] | Catalyst [in mg] | Pph$_3$ [in mg] | Halide [in g] | Acid [in mg] | CO [in bar] | Yield [in %] | Selectivity [in %] |
|---|---|---|---|---|---|---|---|---|---|
| 4 | 24.0 | 100.0 (NMP) | 66 (PdBr$_2$) | 662 | 3.00 (LiBr) | 100 (H$_2$SO$_4$) | 70–80 | 38 | 80 |
| 5 | 24.0 | 100.0 (NMP) | 66 (PdBr$_2$) | 132 | 3.00 (LiBr) | 100 (H$_2$SO$_4$) | 70–80 | 27 | >95 |
| 6 | 24.0 | 100.0 (NMP) | 66 (PdBr$_2$) | 132 | 3.00 (LiBr) | 100 (H$_2$SO$_4$) | 15–20 | 38 | >95 |
| 7 | 24.0 | 100.0 (NMP) | 66 (PdBr$_2$) | 662 | 17.30 (LiBr) | 100 (H$_2$SO$_4$) | 70–80 | 45 | 55 |
| 8 | 24.0 | 100.0 (NMP) | 66 (PdBr$_2$) | 662 | 3.00 (LiBr) | — | 70–80 | 25 | >95 |
| 9 | 24.0 | 100.0 (NMP) | 1000 (30% Pd on C) | 662 | 17.30 (LiBr) | 100 (H$_2$SO$_4$) | 70–80 | 20 | 80 |
| 10 | 24.0 | 100.0 (NMP) | 66 (PdBr$_2$) | 662 | 17.30 (LiBr) | 100 (H$_2$SO$_4$) | 70–80 | 37 | 80 |
| 11 | 24.0 | 100.0 (DMAC) | 66 (PdBr$_2$) | 662 | 3.00 (LiBr) | 100 (H$_2$SO$_4$) | 70–80 | 13 | 95 |
| 12 | 24.0 | 100.0 (NMP) | 66 (PdBr$_2$) | 662 | 3.00 (LiBr) | 100 (H$_2$SO$_4$) | 70–80 | 31 | >95 | cal; in which $R^5$ is a $C_1$–$C_4$-alkyl radical, $R^6$ is a $C_1$–$C_{18}$-alkyl radical and $R^7$ is a $C_6$–$C_{18}$-aryl radical; or in which at least one of the radicals $R^1$, $R^2$, $R^3$ and $R^4$ is substituted by a radical $R^9$, where $R^9$ has the same meaning as $R^1$; or in which at least two of the radicals $R^1$, $R^2$, $R^3$ and $R^4$ are linked to one another and form at least one aliphatic or aromatic ring having 5 to 18 carbon atoms.

2. The process as claimed in claim 1, wherein the radicals $R^1$, $R^2$, $R^3$ and $R^4$ independently of one another are hydrogen, fluorine, methyl, ethyl, methoxy or ethoxy.

3. The process as claimed in claim 1, wherein the dipolar aprotic solvent is dioxane, tetrahydrofuran, N-($C_1$–$C_8$-alkyl) pyrrolidone, N-methylpyrrolidone, ethylene glycol dimethyl ether, ethyl acetate, acetonitrile, tert-butyl methyl ether, dibutyl ether, sulfolane or N,N-dimethylacetamide.

4. The process as claimed in claim 1, wherein the ionic halide is an alkali metal, ammonium or phosphonium halide, halide being chloride, bromide or iodide.

5. The process as claimed in claim 1, wherein the ionic halide is ammonium bromide, lithium bromide, sodium bromide, potassium bromide, tetrabutylphosphonium bromide, ammonium chloride, lithium chloride, sodium chloride, potassium chloride, tetrabutylphosphonium chloride, ammonium iodide, lithium iodide, sodium iodide, potassium iodide, tetrabutylphosphonium iodide, or a combination thereof.

6. The process as claimed in claim 1, wherein the palladium catalyst comprises metallic palladium applied to a support.

7. The process as claimed in claim 1, wherein the palladium catalyst comprises at least one palladium(II) compound.

8. The process as claimed in claim 1, wherein the palladium catalyst comprises $PdCl_2$, $PdBr_2$ or $Pd(OAc)_2$.

9. The process as claimed in claim 7, wherein the palladium catalyst additionally comprises a ligand.

10. The process as claimed in claim 9, wherein the ligand is a phosphine compound.

11. The process as claimed in claim 10, wherein the phosphine compound is triphenylphosphine, tritolylphosphine, bis(diphenylphosphino)ethane, 1,3-bis(diphenylphosphino)propane or 1,4-bis(diphenylphosphino)butane.

12. The process as claimed in claim 1, wherein the palladium catalyst comprises bis(triphenylphosphino)palladium(II) chloride or bis(triphenylphosphino)-palladium(II) bromide.

13. The process as claimed in claim 1, wherein the reaction is carried out in the presence of an inorganic or organic acid having a pKa of less than 5.

14. The process as claimed in claim 13, wherein the acid is sulfuric acid, phosphoric acid, p-toluenesulfonic acid, hexafluoropropanoic acid or trifluoroacetic acid.

15. The process as claimed in claim 1, wherein the reaction is carried out in the presence of a cationic ion exchange resin.

* * * * *